United States Patent

Sommermeyer et al.

[11] Patent Number: 5,945,528
[45] Date of Patent: Aug. 31, 1999

[54] METHOD OF PRODUCING STARCH DECOMPOSITION PRODUCTS

[75] Inventors: Klaus Sommermeyer, Rosbach; Michael Görg, Flortadt; Klaus Henning, Usingen, all of Germany

[73] Assignee: Fresenius AG, Bad Homburg v.d.H., Germany

[21] Appl. No.: 08/809,362

[22] PCT Filed: Sep. 26, 1995

[86] PCT No.: PCT/EP95/03806

§ 371 Date: May 15, 1997

§ 102(e) Date: May 15, 1997

[87] PCT Pub. No.: WO96/10042

PCT Pub. Date: Apr. 4, 1996

[30] Foreign Application Priority Data

Sep. 29, 1994 [DE] Germany .............................. 44 34 877

[51] Int. Cl.⁶ .................................................. C08B 31/00
[52] U.S. Cl. .............................. 536/45; 536/80; 536/102; 536/124; 536/127; 536/128

[58] Field of Search .................................. 536/45, 102, 124, 536/127, 128, 80; 514/60

[56] References Cited

U.S. PATENT DOCUMENTS 5,424,302  6/1995  Nitsch .
5,455,342  10/1995  Redding, Jr. .

FOREIGN PATENT DOCUMENTS

A-33 04 775  1/1992  Germany .
A-41 32 701  4/1993  Germany .

Primary Examiner—James O. Wilson
Attorney, Agent, or Firm—Henderson & Sturm

[57] ABSTRACT

Disclosed is the production of starch decomposition products with a narrow molecular weight distribution, based on the treatment of starch or starch derivatives using high-pressure homogenization. The starch decomposition products are obtained in high yields with a narrow molecular weight distribution.

15 Claims, 2 Drawing Sheets

Translation key:
$M_w$ = mean weight
Tausend = thousand
Durchgänge = passes

Translation key:
Lichtstreusignal = light scatter signal
Elutionsvolumen = elution volume

METHOD OF PRODUCING STARCH DECOMPOSITION PRODUCTS

BACKGROUND OF THE INVENTION

1. Field of the Invention

The invention relates to a method of producing starch decomposition products having a narrow molecular weight distribution by splitting starch or starch derivatives.

Starch decomposition products, especially hydroxyethyl starch (HES), play an important role in many areas of medicine, where they are chiefly used as plasma expanders, but they are also used in dialysis (peritoneal dialysis).

In addition, starch decomposition products are administered for dietetic purposes.

2. Description of the Prior Art

Up until now, both hydrolytically decomposed as well as amylase-decomposed starches have been used to produce HES. For example, an enzymatic method is discussed in DE-C 33 13 600.

The above-mentioned chemical or biochemical methods yield products having a broad molecular weight distribution with a considerable proportion of low-molecular compounds, such as glucose, maltose or oligosaccharides; and by-products occur, for example, in the form of sodium chloride or the enzymes used in the process. These undesired components must then be removed in further process steps, e.g. by precipitation with organic solvents (acetone, isopropanol), or by ultrafiltration. On the one hand this is cost-intensive, and on the other it reduces the yield. However, such purification operations are necessary because usually the aim is to produce a product with the narrowest possible molecular weight distribution and a high degree of purity.

DE-A-41 32 701 describes such a method in which starch or starch derivatives are treated with ultrasound in an aqueous mixture (dispersions, suspensions or solutions). The purpose is to adjust the desired mean molecular weight at the desired level, as a function of the processing time and the intensity of exposure to the ultrasonic radiation, while obtaining a very narrow molecular weight distribution, in the practically total absence of undesired low-molecular components.

However, this latter method is technically very complex and in addition requires a high input of energy to split the starch.

DE-A-33-04 775 describes a method for the depolymerization of polysaccharides which can be used only for solutions of polysaccharides having a helix structure, but not for solutions of polysaccharides having a single-chain structure or an aggregated conformation. Furthermore, it has been discovered that ultrasonic depolymerization is not suitable for depolymerization of large batches on an industrial scale.

BRIEF SUMMARY OF THE INVENTION

According to WO 93/21008, starch is subjected to one or more abrupt changes in pressure in a chamber (piston device) in order to modify its physical properties. This method involves the use of a "Pascalisator" (high-pressure treatment apparatus). Only static pressure is exerted on the sample or liquid. In this method, no reduction of molecular weight is achieved. This method is therefore not suitable for obtaining a starch decomposition product with a narrow molecular weight distribution.

It is therefore the purpose of the invention to make available a method of the type described at the beginning which is technically simple and in addition requires relatively little energy to split the starch, while avoiding as far as possible the formation of undesired low-molecular starch components and while producing the highest possible yield of decomposition products.

According to the invention, this task is accomplished by using high-pressure homogenization to split the starch.

DETAILED DESCRIPTION OF THE INVENTION

Figure 1:
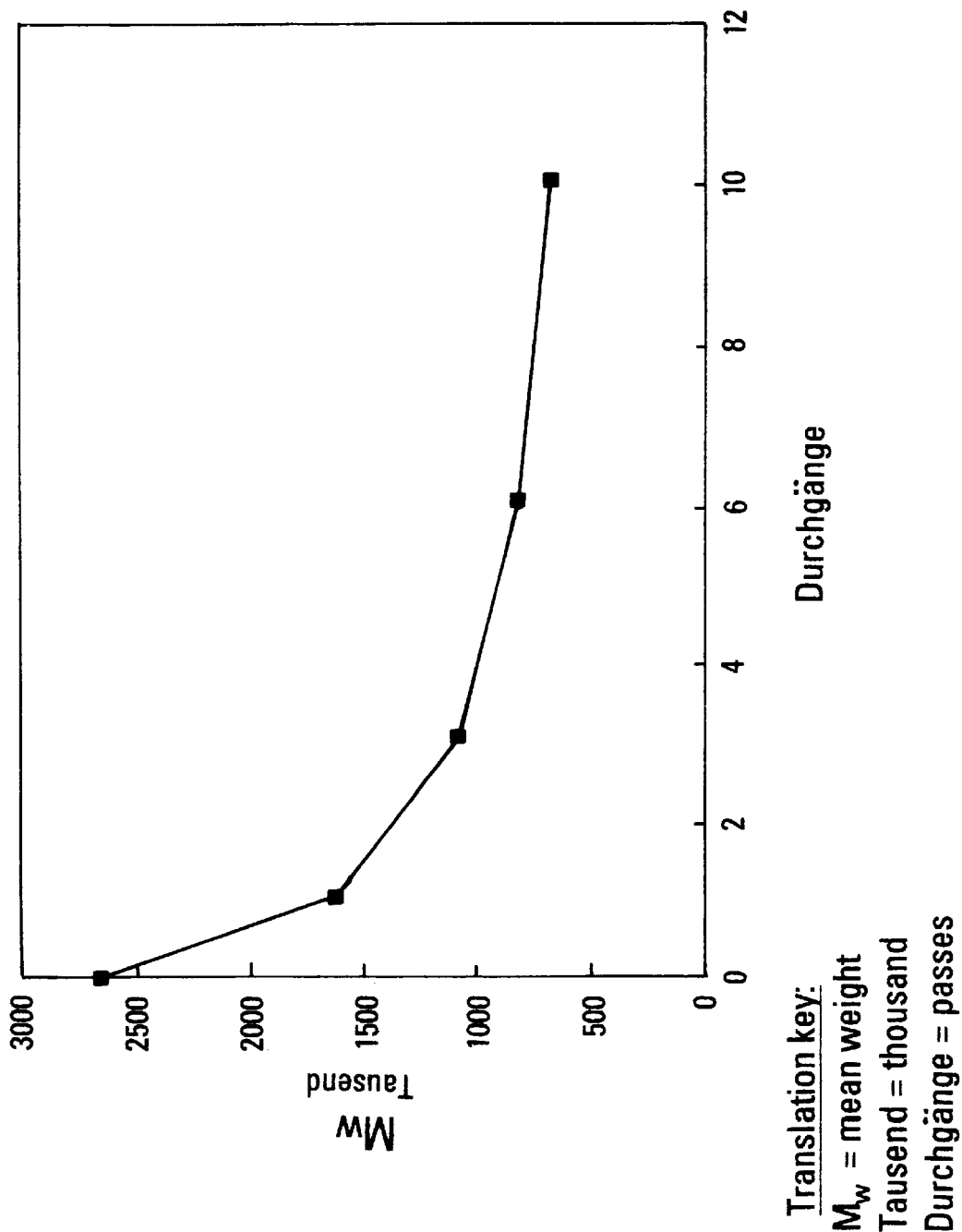
FIG. 1 is a graph showing a decrease in mean molecular weight as a function of passes

Compared with the ultrasonic technique, with which an expert in the field is familiar, the method according to the invention offers the advantage that the technology to be used is already widely employed for the manufacture of emulsions or dispersions and therefore is already available in most processing plants, so that the investment costs are relatively low. In addition, high-pressure homogenization consumes less energy than the ultrasonic technique.

In the homogenization method used according to the invention, the liquid is forced by high-pressure pump units through a precision disintegration valve. The pressure required (500→2000 bar) and the number of passes depend on the desired molecular weight. In this valve, the material passes through a high-performance cavitation zone in which the high-molecular chains are destroyed or broken up under the action of intense local tensile, compressive or shear stresses. According to the invention, the aforementioned treatment process breaks up the long-chained structure of the starch or starch derivatives.

Compared with the method described in DE-A-33 04 775, the method according to the invention has the surprising advantage that branched-chain polysaccharides not having a helix structure may also be broken down; that is not the case in the state-of-the-art method.

According to the invention, it is possible to adjust a desired mean molecular weight (mean weight $M_w$) by varying the pressure applied, also by varying the number of treatments, the temperature, the concentration of the starch or the starch derivatives, and the pH value, while achieving a narrow molecular weight distribution down to molecular weights in the order of 100,000 daltons, in the absence of undesired low-molecular components. This method gives yields of almost 100%.

In addition, this method does not require any addition of acids, as is necessary for example in the case of acid hydrolytic decomposition, nor the addition of enzymes, as is required for example in the case of enzymatic decomposition; consequently, any further processing steps, such as precipitation with organic solvents or diafiltration, are kept to a minimum.

Preferably native starch, partially hydrolyzed starch or derivatives thereof, are used as the starting material, said starch consisting of amylose-free or low-amylose (<5% amylose) amylopectin. Advantageously corn starch, rice starch and/or sorghum starch are used.

The starch derivatives are partially hydrolyzed starch or other starch derivatives, for example an hydroxyalkyl or alkoxyalkyl starch derivative, especially a hydroxyethyl starch derivative. The partially hydrolyzed starches may also be obtained by acid hydrolysis and/or enzymatic hydrolysis.

The starch or starch derivatives may be used in the form of aqueous dispersions, suspensions or solutions. By suspension is meant a dispersion of insoluble, non-colloidal starch particles. The solutions used here contain starch or starch derivatives dissolved in water. On the other hand, however, colloidal mixtures of starch or starch derivatives in water may be used. Following gelatinization, such aqueous solutions may contain 5–40 wt.-% of starch or starch derivatives, and the latter should have a mean molecular weight of more than 200,000 daltons. On the other hand, 5–60 wt. % aqueous suspensions of starch or starch derivatives may also be used.

Starch derivatives which were previously hydrolytically or enzymatically split may undergo high-pressure homogenization without prior isolation in an aqueous dispersion or solution,.

High-pressure homogenization can be carried out in a known manner and with commercially available equipment suitable for the purpose.

The homogenization conditions usually depend on the type of starting material, the type of reaction mixture and in particular the targetted result, which is predetermined by the desired mean molecular weight of the starch end product.

Homogenization is usually carried out at a temperature of 5–95° C., although a room temperatuire of approx. 20° C. is preferred.

Homogenization is carried out at pressures of 500–2000 bar, although pressures beyond the limit pressure of 2000 bar may also be used.

Usually, after several pressure treatments (passes) in the high-pressure homogenizer, a saturation level is reached below which saturation no longer falls. The term "pass" is understood here to mean a single instance of forcing the test material through the gap. The higher the pressure, the greater the decomposition of the starch polymers, i.e. with increasing pressure smaller mean molecular weights are obtained. The advantage of the method according to the invention is that a molecular weight can be relatively easily set by the number of passes, which is determined beforehand; this is in contrast to acid hydrolysis which must be permanently monitored by viscometric means.

Thus, by selecting the conditions, it is relatively easy to obtain a mean, target molecular weight without expensive monitoring of the viscosity.

The starch decomposition products produced by the method according to the invention may be advantageously used to produce high yields of etherified or esterified starch (HES or acetyl starch). These starch decomposition products (especially HES) are used in medical applications, especially as volume expanders.

A further object of the invention is the use of starch decomposition products, produced according to the method of the invention, in pharmaceutical formulations for clinical and preferably parenteral applications. Furthermore, the starch decomposition products produced by the method according to the invention may also be used in pharmaceutical formulations for peritoneal dialysis or as blood plasma expanders.

If low molecular constituents arising from previous processing steps have to be removed from the decomposition products according to the invention, this can of course be accomplished by means of the known method of diafiltration, using a suitable choice of membranes. Finally, the starch decomposition products which are usually in solution can also be dried by the usual methods (concentration of the solution in a vacuum or freeze drying and subsequent spray drying).

Figure 2:
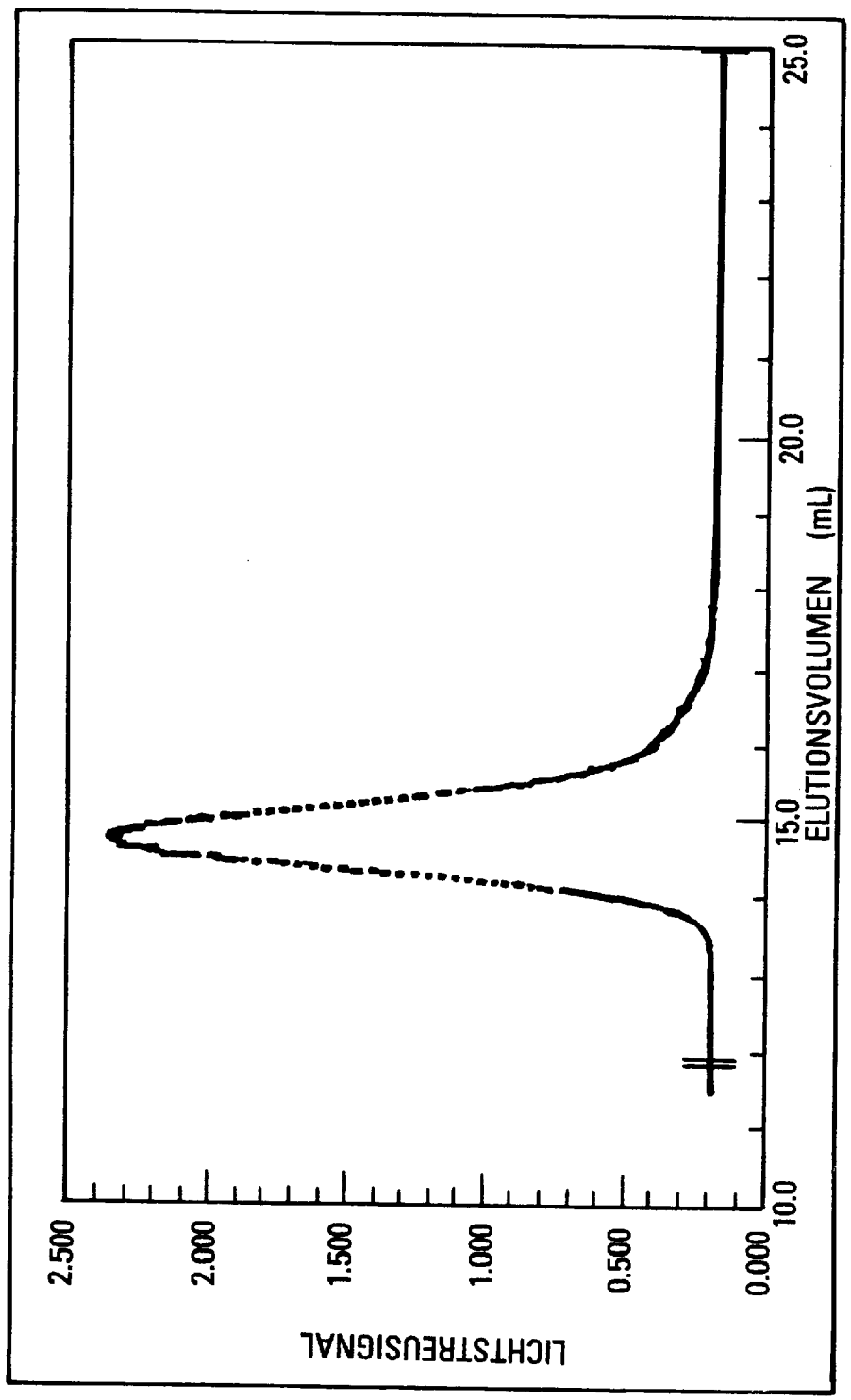
FIG. 2 is a graph showing molecular weight distribution in the case of exclusion chromatography.

FIGS. 1 and 2 illustrate the effect of high-pressure homogenization used to produce HES 450 (mean molecular weight=450,000 daltons). FIG. 1 shows the decrease in mean molecular weight as a function of the number of passes, while FIG. 2 shows the molecular weight distribution in the case of exclusion chromatography by plotting the light scatter over the elution volume (mean weight).

EXAMPLE

The invention is explained by the following example.

Partially decomposed waxy corn starch having a mean molecular weight of 2,689,000 daltons, was converted with ethylene oxide, in a known manner, into HES. A 15 wt. % solution of this HES product in unpurified form, was homogenized altogether 10 times in a high-pressure homogenizer (manufacturer: APV-Gaulin, Lübeck) at temperatures of 50–70° C. and a pressure of approximately 1600 bar. After 10 passes, a molecular weight (mean weight $M_W$) of approximately 670,300 daltons was found, as illustrated in FIG. 1.

What is claimed is:

1. A method for producing starch decomposition products, said method comprising splitting at least one starch by subjecting said starch to a high pressure homogenization procedure comprising forcing said starch through a high-pressure precision disintegration valve within a temperature range of about 5° C. to about 95° C., at a pressure greater than 500 bar.

2. A method according to claim 1, wherein the high-pressure homogenization procedure is repeated a sufficient number of times until desired mean molecular weight $M_W$ is attained.

3. A method according to claim 1 wherein said starch is selected from the group consisting of partially hydrolyzed starch, obtained by acid hydrolysis and partially hydrolyzed starch obtained by enzymatic hydrolysis.

4. A method according to claim 3, wherein said starch comprises a native starch.

5. A method according to claim 4, wherein said native starch comprises an aqueous dispersion of a native starch produced by gelatinization.

6. A method according to claim 3, wherein a reaction mixture obtained after hydrolysis or etherification undergoes high-pressure homogenization without prior isolation of the reaction product.

7. A method according to claim 1, wherein the high-pressure homogenization is carried out at a temperature in a temperature range of about 5–95° C.

8. A method according to claim 1, wherein the high-pressure homogenization is carried out at a pressure within a range of at least about 500 bar to about 2000 bar.

9. A method according to claim 1, wherein said starch and is in a form selected from the group consisting of an aqueous dispersion, a suspension, and a solution.

10. A method according to claim 9, wherein said starch is selected from the group consisting of an aqueous dispersion of a partially hydrolyzed starch and an aqueous dispersion of a partially hydrolyzed starch derivative.

11. A method according to claim 3, wherein said starch is selected from the group consisting of partially hydrolyzed starch obtained by acid hydrolysis and partially hydrolyzed starch obtained by enzymatic hydrolysis comprises a mean molecular weight of greater than about 2,000,000 daltons.

12. A method according to claim 4, wherein said native starch comprises amylopectin.

13. A method according to claim 5, wherein said aqueous dispersion of a native starch produced by gelatinization is present in an amount within the range of about 5 wt. % to about 60 wt. %.

14. A method according to claim 10, wherein said starch is selected from the group consisting of an aqueous dispersion of a partially hydrolyzed starch and an aqueous dispersion of a partially hydrolyzed starch derivative is present in an amount within a range of about 5 wt. % to about 40 wt. %.

15. A method accordingly to claim 1, wherein said temperature is about room temperature.

* * * * *